United States Patent [19]

Dill et al.

[11] 4,370,242

[45] Jan. 25, 1983

[54] DEVICE FOR AND A METHOD TO SEPARATE ORIENTABLE OR DEFORMABLE PARTICLES

[75] Inventors: Ken A. Dill, Mountain View; Bruno H. Zimm, La Jolla; Richard H. Shafer, Mill Valley, all of Calif.

[73] Assignee: The Regents of the University of California, Berkeley, Calif.

[21] Appl. No.: 193,428

[22] Filed: Oct. 3, 1980

[51] Int. Cl.$^3$ .............................................. B01D 43/00
[52] U.S. Cl. ................................. 210/787; 210/512.3
[58] Field of Search ............ 210/787, 800, 801, 512.1, 210/512.3, 533–535

[56] References Cited

U.S. PATENT DOCUMENTS

| | | | |
|---|---|---|---|
| 1,260,135 | 3/1918 | Blomfield | 210/512.3 |
| 1,885,735 | 11/1932 | Laughlin | 210/787 |
| 3,718,259 | 2/1973 | Harrison | 210/787 |
| 3,897,414 | 7/1975 | Albertsson | 260/211.5 R |
| 4,030,707 | 6/1977 | Moreton | 259/8 |

OTHER PUBLICATIONS

Dill, "Theory For The Separation of Very Large DNA Molecules by Radial Migration", *Biophysical Chemistry* 10, (1979), 327-334, N. Holland Pub. Co., Amsterdam.

Shafer et al., "Radial Migration of DNA Molecules in a Cylindrical Flow I", *Biophysical Chemistry* 2, (1974), 180-184, N. Holland Pub. Co., Amsterdam.

Shafer, "Radial Migration of DNA Molecules in a Cylindrical Flow II", *Biophysical Chemistry* 2, (1974), 185-188, N. Holland Pub. Co., Amsterdam.

Dill et al., "Radial Migration of DNA Molecules in a Cylindrical Flow III", *Biophysical Chemistry* 4, (1976), 51-54, N. Holland Pub. Co., Amsterdam.

Dill et al., "A Rheological Separator For Very Large DNA Molecules", *Nucleic Acids Research*, vol. 7, No. 3, (1979), 735-749.

*Primary Examiner*—Ivars C. Cintins
*Attorney, Agent, or Firm*—Phillips, Moore, Lempio & Finley

[57] ABSTRACT

A device comprised of a cone-shaped container and a rotatable concentric cone positioned in the container results in migration of orientable or deformable particles such as large polymer molecules toward the center of the container when the concentric cone is rotated relatively slowly in a solution containing such particles.

16 Claims, 6 Drawing Figures

DEVICE FOR AND A METHOD TO SEPARATE ORIENTABLE OR DEFORMABLE PARTICLES

The Government has rights in this invention pursuant to Grant No. RG-25 awarded by the National Science Foundation.

BACKGROUND OF THE INVENTION

This invention relates to a device and a method for the separation of orientable or deformable particles. In particular it relates to a device which uses a radial migration technique to separate orientable or deformable particles such as large polymer molecules.

It has been found that separation of large polymer molecules becomes increasingly difficult as the molecular weight increases. Such conventional techniques as sedimentation through the use of a centrifuge or by gel electrophoresis are not satisfactory with polymer molecules of very high molecular weight. In particular, random coiled DNAs have anomalous sedimentation coefficients making separation impractical in the centrifuge. The inhomogeneity of the gel structure limits gel electrophoresis to separations of molecules which have a molecular weight less than $5 \times 10^8$ Daltons, with resolution at the upper end being relatively poor. While some efforts have been made in automated sorting of individual chromosomes, the procedure is a one-at-a-time effort which militates against its practicality for preparation of large quantities of such polymer molecules as DNA.

The deformability of very large macromolecules such as DNA and other molecules of chromosomal size has been at the heart of the separation problems mentioned above. This deformability manifests itself in dilute solutions of the macromolecules as viscoelasticity, a rather unusual set of properties when compared with ordinary viscous solutions. One property is the "Weissenberg effect." The Weissenberg effect occurs when a viscoelastic liquid is sheared in the gap between two moving surfaces such as concentric cylinders. In an ordinary viscous solution, the pressure is highest at the outside cylinder because the liquid is thrown to the outside by inertia. When a viscoelastic liquid is similarly sheared, the liquid will creep up the inside cylinder, and the pressure will be highest on the inside cylinder. A simple explanation is that the very large macromolecules act like elastic bands moving along circular flow lines between the cylinders. Since the relative motion of the two cylinders applies a shear force in the solution which stretches the molecules, there is a small component of tension in the molecule that acts to produce on the molecule an inwardly directed radial force. The sum of these radial forces from all the polymer molecules gives the Weissenberg pressure.

While the Weissenberg effect has been known for a long time, no practical use of the migration accompanying the Weissenberg effect has been made. Concurrently, the increase in research in large and very large macromolecules, with particular emphasis on DNA and the like, coupled with the knowledge that single DNA molecules may constitute whole chromosomes, has resulted in efforts to solve separation problems related to experimentation with such macromolecules.

It is therefore an object of this invention to provide a device for separation of large to very large macromolecules utilizing a radial migration principle.

It is another object of this invention to provide a method for separation of large and very large macromolecules through the principles of radial migration.

It is also an object of the invention to provide a separation device for large and very large macromolecules that is relatively inexpensive.

It is still another object of this invention to provide a device that separates large and very large macromolecules so that the user is confident that separation of the molecules has occurred.

DISCLOSURE OF THE INVENTION

The present invention is directed to overcoming one or more of the problems as set forth above and to meeting the objects set forth above and such other objects as may be apparent from the reading of the description and the appended claims.

In one aspect of the invention, a separator is comprised of a container having a first interior surface. A member defining a surface is positionable so that the member surface is directed downwardly toward the first interior surface. The member surface defines an axis, and the member is rotatable in the aforesaid container about an axis coincident with the member surface axis. Finally, the container defines an outlet at a position generally on an extension of the axis of the member surface.

In another aspect of this invention, a method is disclosed for separating large polymer molecules which includes the steps of placing a solution containing a quantity of large polymer molecules in a container having a rotatable member therein. The second step consists of rotating the member slowly to create a shear force between the member and the container, while the third step is one of draining off a portion of the solution through a drain located in the container.

Separation of large and very large macromolecules such as polymers of the DNA type have presented unique problems to the normal sedimentation or gel electrophoresis methods of separation. Accordingly, this invention utilizes the deformability of the large molecules to advantage by utilizing the inward radial migration of the molecules resulting from the shear force of rotation of one cone relative to another cone.

BEST MODE OF CARRYING OUT THE INVENTION

Figure 1:
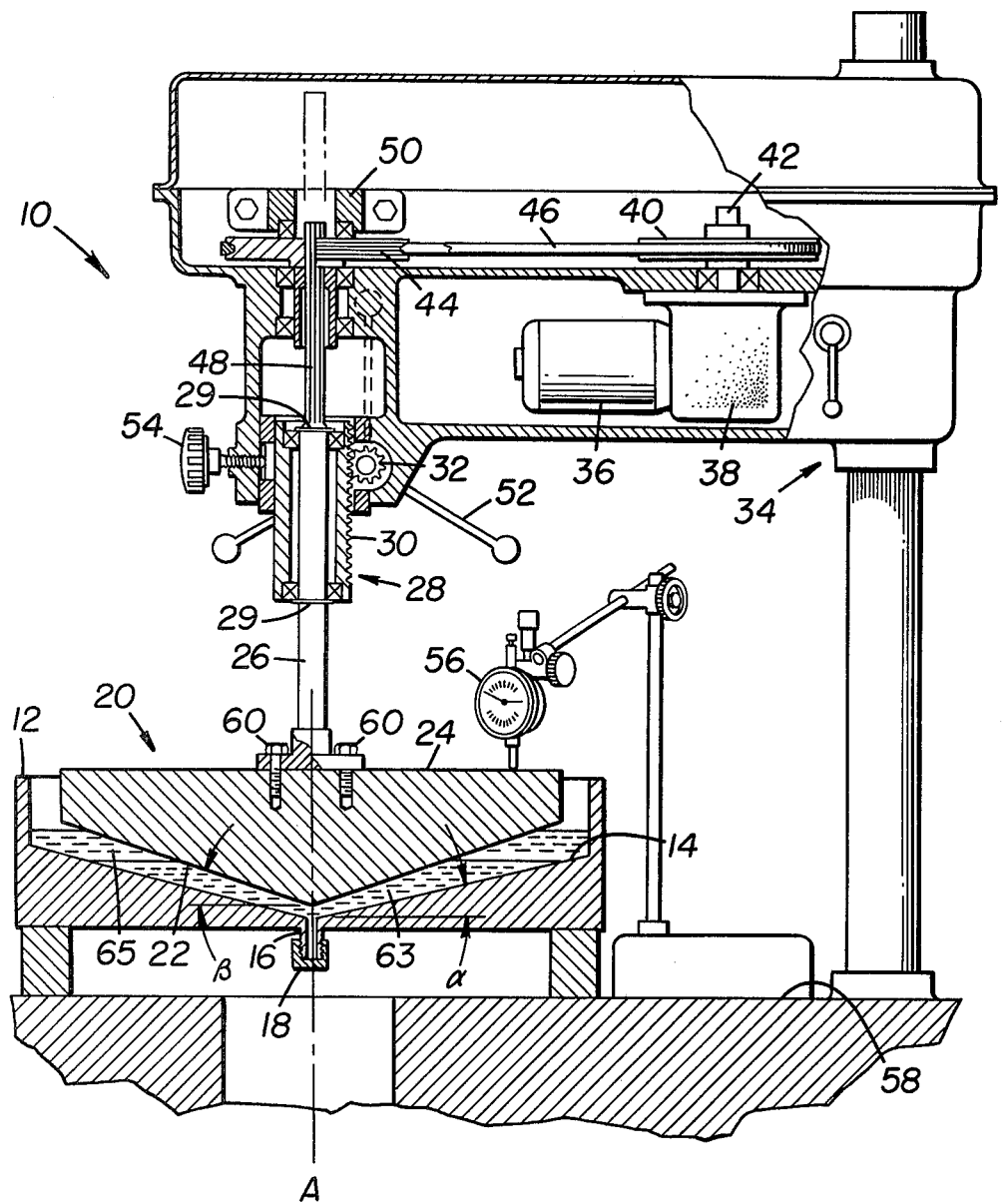
FIG. 1 is a diagram partly in section of one embodiment of this invention showing the concentric cone structure there.

Referring to FIG. 1, a separator 10 that may be used for the separation of deformable particles or orientable particles which includes large polymer molecules such as DNA is shown partly in section and partly schematically. Since this invention is particularly applicable to the separation of large polymer molecules, the following specification will be directed to such deformable particles. Separator 10 consists of a container 12 having an interior surface 14 which may be generally a flat surface of revolution, but is preferably conical as shown in FIG. 1. At the apex of the conical interior surface 14 is a drain of efflux tube 16 that forms a means to withdraw fluids from container 12. Efflux tube 16 is fitted with a cap 18 to prevent leakage of fluids positioned in container 12.

A member 20 is positionable in container 12 so that member 20 and container 12 may rotate relative to each other about an axis A that passes through efflux tube 16. In the preferred embodiment, member 20 is rotatable relative container 12. Rotatable member 20 has a lower surface 22 which may also be generally a surface of revolution, but is preferably cone shaped with the apex at the cone on axis A and juxtaposed with interior surface 14. The two cone-shaped surfaces 14 and 22 in the preferred embodiment are such that the angle $\alpha$ formed by the cone-shaped first interior surface 14 and a plane normal to axis A is less than the angle $\beta$ formed by cone-shaped lower surface 22 and a plane normal to axis A. Angle $\alpha$ may, for example, be less than 11° and is preferably 10°. Angle $\beta$ in the preferred embodiment should therefore be greater than 11° and preferably is 13.7°.

The opposite side of rotatable member 20 is preferably flat, such as surface 24. The reason for the flat surface will become apparent in the ensuing discussion. Extending upwardly from surface 24 is a shaft 26 which is affixed to rotatable member 20. Shaft 26 is rotatable in a bearing 28 which has formed thereupon a rack 30. Rack 30 is driven by a pinion 32 mounted on a stand 34 as shown in FIG. 1. Bearing 28 may be fixed relative to shaft 26 by snap rings 29 or other appropriate means.

Means, in the form of an electric motor 36, are provided for rotating rotatable member 20. Electric motor 36 drives a speed reduction gear box 38 which, in turn, drives a pulley 40 by means of shaft 42. An example of such a drive mechanism is found in an ordinary drill press.

Pulley 40 drives a second pulley 44 by means of a belt 46. Second pulley 44 is splined to shaft 26 at its upper end 48 so that pulley 44 will drive shaft 26, which in turn drives the rotatable member 20. Appropriate bearing structure 50 is provided to ensure the alignment of pulley 44 with pulley 40 during upward and downward movement of shaft 26. Such upward and downward movement of shaft 26, as previously indicated, is accomplished by rotation of pinion 32, which is readily rotated through a lever 52. Since the positioning of rotatable member 20 relative to container 12 is important, a locking mechanism such as a set screw 54, may be used. Set screw 54 is threadably engaged in stand 34 such that rotation of set screw 54 results in frictional engagement with bearing 28 with sufficient force to lock bearing 28 and thus, shaft 26, and rotatable member 20 in the desired position.

As was previously stated, the positioning of rotatable member 20 relative to container 12 may be important. Accordingly, the separator 10 is equipped with a means for locating the rotating member 10 relative the container 12. Such means includes a conventional dial indicator gauge 56 which may be positioned on surface 58 of stand 34.

Finally, it should be noted that rotatable member 20 may be removed for cleaning from spindle 26. This may be accomplished by bolts 60 or other appropriate means such as a chuck (not shown).

Figure 4:
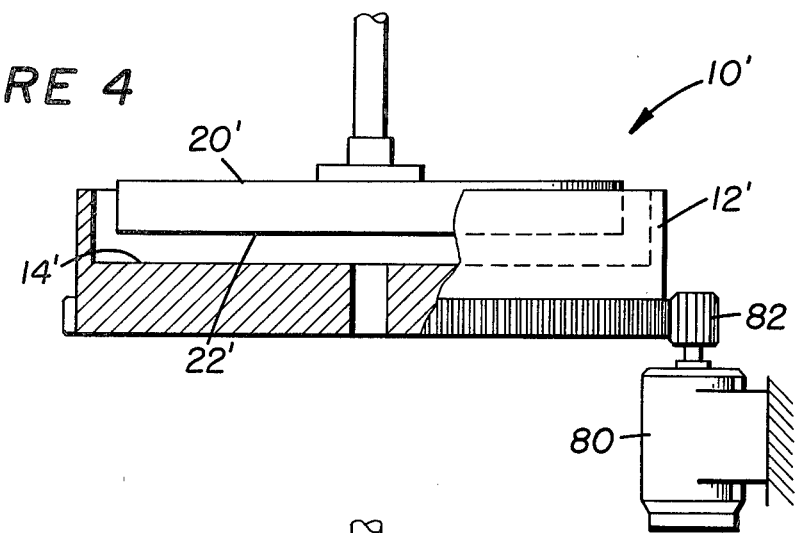
FIG. 4 is an alternate embodiment of the separator disclosed herein.

An alternate embodiment 10' of the separator is shown in FIG. 4. In this embodiment container 12' is rotatable relative to member 20'. A drive mechanism 80 may use a friction or gear drive 82 to accomplish this rotation. In the embodiment shown in FIG. 4, interior surface 14' and surface 22' are both flat, but remain in their same relative orientations. It should be understood that these surfaces may also be used on the primary embodiments in lieu of the conical surfaces.

Figure 5:
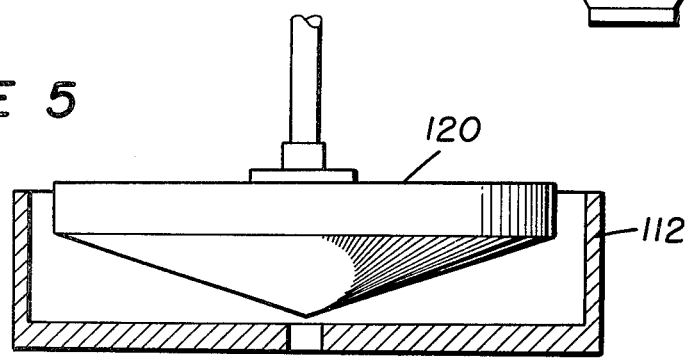
FIG. 5 is still another embodiment of the separator.
Figure 6:
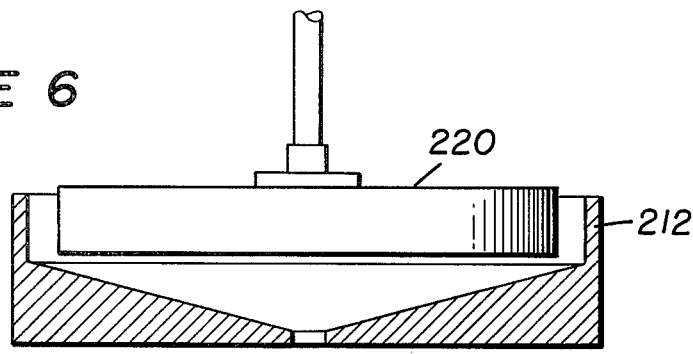
FIG. 6 is a fourth embodiment of the separator.

FIGS. 5 and 6 illustrate various other combinations. In FIG. 5, member 120 has a cone-shaped lower surface while container 112 has a flat interior surface. In FIG. 6, member 220 has a flat lower surface with container 212 having a conical interior surface. In both these embodiments, the one member rotates relative to the other member.

INDUSTRIAL APPLICABILITY

Figure 2:
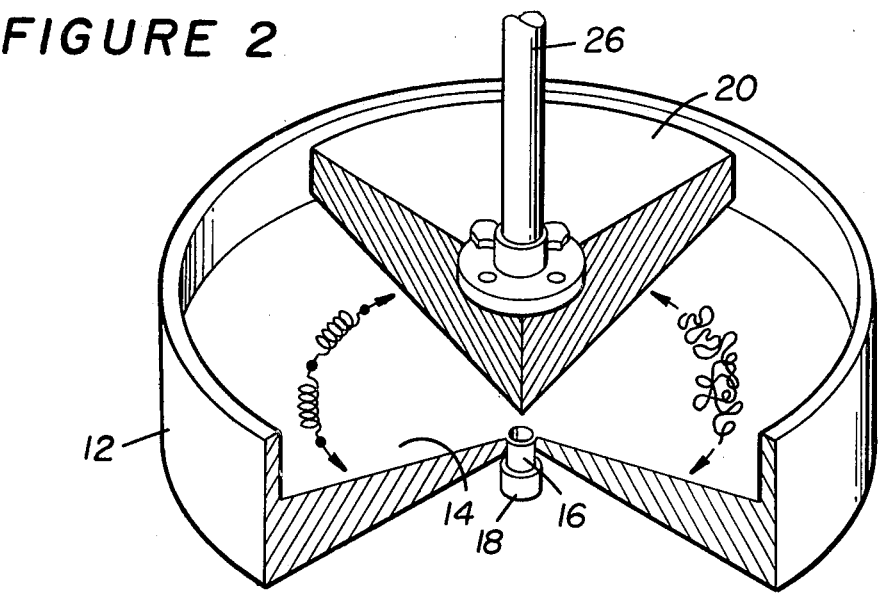
FIG. 2 is a perspective view, partly cut away, showing the same invention as in FIG. 1.

Referring now to FIG. 1 and FIG. 2, a brief description of the applicability of this invention to the field of separation of a mixture of macromolecules having various molecular weights will be described. The material to be separated should be contained in a viscous solution. The solvent need not be discussed except to say that it should preferably have a relatively low density.

A quantity 63 of a "pure" solvent without any material to be separated and with a relatively high density is placed in container 12 with rotatable member 20 moved upwardly by means of the rack and pinion 30 and 32, respectively. It should be understood that "pure" is used herein to denote a solvent not containing any of the macromolecules to be separated. The movable member 20 is then moved downwardly to come into contact with surface 14 and then moved back upwardly a predetermined amount. 0.002 inches (0.0508 mm.) has been found adequate to permit flow of the material through efflux tube 16 after separation has been achieved. This measurement is attained through the use of dial indicator 56 in the conventional manner. Other ways of introducing the solvent may be used such as by introduction through the efflux tube.

After positioning the movable member 20, a second quantity 65 of the low density solution containing the macromolecules to be separated is layered on top of the relatively high density "pure" solvent. Should shear sensitivity of the DNA being separated be a problem, a syringe pump may be used to slowly position the solution. While a gradient is preferred, the gradient need not necessarily be a stepped gradient as just described.

With the cones set and the solution in place, it is appropriate to take a sample or fraction through efflux tube 16. Experience has shown that in the separation of large polymer molecules, about 0.4 ml of solution is adequate. It may take upwards of thirty (30) minutes to collect the sample by dripping through the efflux tube, due to the viscosity of the solution. Efflux tube 16 should then be plugged with plug 18 or other appropriate means and the top cone or rotatable member 20 set spinning at a slow speed. This speed should increase to the operating speed (approximately 25 rpm) within a reasonable time. The rotatable member is then spun at or about the operating speed for an appropriate time, at which time rotation is reduced to about ten percent of the operating speed in order to collect the fractions through efflux tube 16. During the separation phase, the heaviest macromolecules will migrate through the relatively high density solution to the center of the device while the lighter macromolecules will layer themselves outwardly from the center in concentric rings, thus permitting relatively pure fractions to be collected.

Figure 3:
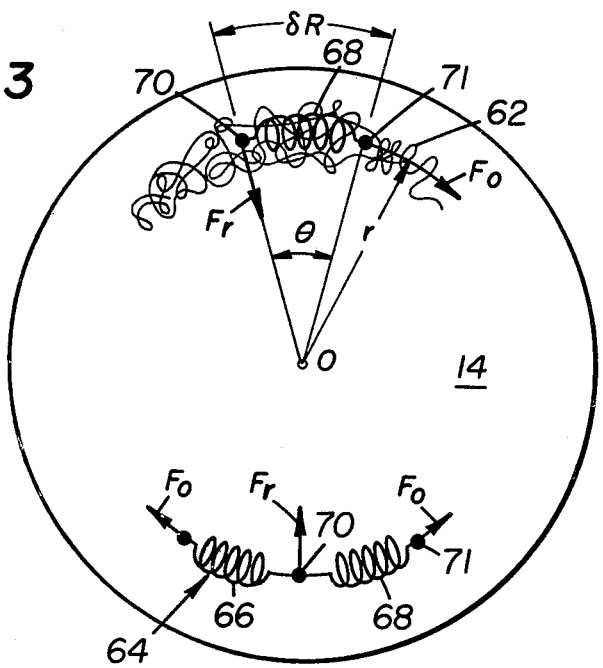
FIG. 3 is a schematic diagram of the forces inherent in the separator during operation.

It is appropriate to review the theory behind the separator in order to understand the inward radial migration of the large molecules. Reference is made to FIG. 3 wherein a very large molecule such as a DNA molecule is represented at 62. It should be understood that molecule 62 is greatly enlarged in order to better understand the principle involved. Opposite molecule 61 is a schematic diagram of a DNA molecule 64. This schematic DNA molecule 64 which is illustrative of very large polymer molecules, illustrates the Weissenberg effect utilized in the separator. Specifically, each large or very large macromolecule is separable into a series of coil-like springs 66 and 68 (only two of which are shown in this illustration). The coil-like springs 66 and 68 which together represent a DNA molecule are fixed together in a chain at end points such as point 70 and again at point 71. These same points in the coil-like spring 68 are represented on molecule 62 schematically. This coil-like spring 68 has a radius $\delta R$ over an angle $\theta$ for the molecule 62 located at a radius r from the center O of rotatable member 20. The shear force present when the rotatable member 20 is turned with container remaining stationary, causes a "stretching" of springs 66 and 68 and the other springs representative of the DNA molecule such that a force $F_o$ is present along an arc generally concentric with the rotation of the rotatable member 20. The plurality of force factors $F_o$ results in an inwardly directed force $F_r$ represented schematically at each node point 70 connecting the various "spring-like" elements of the molecule. As a result of this resultant force $F_r$, over a period of time, the molecule 62 will move inwardly toward the center of the rotatable member 20. It should be apparent to those skilled in the art that the molecular weight of molecule 62 is a determining factor on the rate of migration inwardly toward the center O. Therefore, the heavier molecules can be expected to move more rapidly toward center O than the lighter molecules. Thus, by fractions taken through efflux tube 16 after periods of time of rotation of rotatable member 20, the various representative samples of very large molecules such as DNA molecules can be separated.

The embodiments depicted in FIGS. 4, 5, and 6 operate generally as indicated above.

These and other objects, aspects, and advantages of this invention can be obtained from a study of the drawings, the disclosure, and the appended claims.

What is claimed is:

1. A separator comprising:
   a container having a first interior surface;
   a member defining a continuous surface, said member selectively positionable in said container so that said member surface is adjacent to said first interior surface, said member defining an axis, said member and said container relatively rotatable one to the other about said axis; and
   said container defining a drain hole, said drain hole generally on the extension of the axis of the member surface.

2. The separator of claim 1 further including:
   means for rotating said rotatable member about said axis of said member surface.

3. The separator of claim 1 wherein said member surface is cone-shaped with said axis coincident with the axis of said cone-shaped member surface, the apex of said cone-shaped surface downwardly directed.

4. The separator of claim 3 wherein said first interior surface is cone-shaped, said cone-shaped first interior surface making a lesser angle with the plane normal to said axis of the rotatable cone-shaped surface than the angle said rotatable cone-shaped surface makes with a plane normal to its axis.

5. The separator of claim 4 wherein a generatrix of said cone-shaped first interior surface subtends an angle of less than 11° with a plane normal to the axis of said rotatable cone-shaped surface.

6. The separator of claim 5 wherein a generatrix of said cone-shaped first interior surface subtends an angle of greater than 11° with a plane normal to the axis of said rotatable cone-shaped surface.

7. The separator of claim 6 further including means for adjustably spatially separating the rotatable cone-shaped member from the container.

8. The separator of claim 7 wherein the means for spatially separating the rotatable cone-shaped member from the container includes means for measuring the separation between the rotatable cone-shaped member and the container.

9. The separator of claim 1 wherein the member and the container are movable toward and away from one another.

10. The separator of claim 9 further including means for rotating said member at a rate less than 100 rpm.

11. A method for separating deformable particles comprising the steps of:
    placing a solution containing a quantity of deformable particles in a container, the container having a rotatable member therein, said rotatable member having a lower surface formed of a surface of revolution;
    rotating the rotatable member slowly to create a shear force;
    allowing said particles to migrate toward the center of said container;
    draining off a portion of the solution through a drain located at the apex of the lower cone following a predetermined period of time of rotation.

12. The method of claim 11 including, before the step of draining, the step of decreasing the rate of rotation of the rotatable member.

13. The method of claim 12 wherein the step of placing the solution containing a quantity of deformable particles in the container includes the following substeps:
    placing a relatively higher density solvent in a container;
    placing the rotatable member in said container;
    layering a second quantity of a relatively lower density solvent containing a quantity of deformable particles on top of said relatively high density solvent.

14. A method for separating deformable particles comprising the steps of:
    placing a relatively high-density solvent in a container;
    placing a rotatable member having a lower surface formed of a surface of revolution in said container;
    layering a second quantity of relatively lower-density solvent containing a quantity of deformable particles on top of said relatively high-density solvent;
    rotating the rotatable member slowly to create a shear force;
    allowing said particles to migrate toward the center of said container;

decreasing the rate of rotation of the rotatable member;

draining off a portion of the solution through a drain located at the apex of the lower cone following a predetermined period of time of rotation.

15. The method of claim 14 wherein the step of placing the rotatable member in the container contains the following substeps:

placing the rotatable member in said container so that the center of the rotatable member contacts the inner surface of the container;

separating the rotatable member a predetermined amount from the inner surface of the container.

16. A separator comprising:

a container having a first interior surface;

a member defining a continuous surface of revolution, said member selectively positionable in said container so that said surface of revolution is adjacent to said first interior surface, said member defining an axis, said member and said container relatively rotatable one to the other about said axis; and said container defining a drain hole, said drain hole generally on the extension of the axis of the member surface.

* * * * *